US011806486B2

(12) United States Patent
Kato

(10) Patent No.: US 11,806,486 B2
(45) Date of Patent: Nov. 7, 2023

(54) MEDICAL APPARATUS COMPRISING A BENDABLY DEFORMABLE PORTION

(71) Applicant: CANON KABUSHIKI KAISHA, Tokyo (JP)

(72) Inventor: Takahisa Kato, Brookline, MA (US)

(73) Assignee: Canon Kabushiki Kaisha, Tokyo (JP)

(*) Notice: Subject to any disclaimer, the term of this patent is extended or adjusted under 35 U.S.C. 154(b) by 961 days.

(21) Appl. No.: 16/359,805

(22) Filed: Mar. 20, 2019

(65) Prior Publication Data
US 2019/0217062 A1 Jul. 18, 2019

Related U.S. Application Data

(62) Division of application No. 14/403,918, filed as application No. PCT/JP2013/064562 on May 21, 2013, now abandoned.

(30) Foreign Application Priority Data

May 31, 2012 (JP) ................................. 2012-124499

(51) Int. Cl.
A61M 25/01 (2006.01)
A61B 1/005 (2006.01)
A61B 5/24 (2021.01)
A61B 5/00 (2006.01)
A61B 17/00 (2006.01)

(52) U.S. Cl.
CPC ....... A61M 25/0147 (2013.01); A61B 1/0057 (2013.01); A61B 5/24 (2021.01); A61B 5/6852 (2013.01); A61B 17/00234 (2013.01); A61B 1/0052 (2013.01); A61B 2017/00305 (2013.01); A61B 2017/00323 (2013.01)

(58) Field of Classification Search
None
See application file for complete search history.

(56) References Cited

U.S. PATENT DOCUMENTS

| 3,754,757 A | * | 8/1973 | Bowen | ..................... A63B 7/08 482/34 |
| 5,466,082 A | * | 11/1995 | Sherar | ..................... F16G 11/08 403/2 |
| 2009/0192357 A1 | * | 7/2009 | Torii | ..................... A61B 1/0052 600/149 |

FOREIGN PATENT DOCUMENTS

JP 2003339630 A * 12/2003

OTHER PUBLICATIONS

English-language machine translation of JP-2003339630-A, www.patents.google.com, printed on Feb. 16, 2022, 7 pages (Year: 2022).*

* cited by examiner

Primary Examiner — Matthew Kremer
(74) Attorney, Agent, or Firm — Canon U.S.A., Inc. IP Division

(57) ABSTRACT

A medical apparatus includes a bendably deformable portion, a deforming-force-transmitting mechanism that is connected to a part of the bendably deformable portion, and an operation portion that applies a deforming force or a shape retaining force to the bendably deformable portion by controlling a tension applied to the deforming-force-transmitting mechanism.

5 Claims, 8 Drawing Sheets

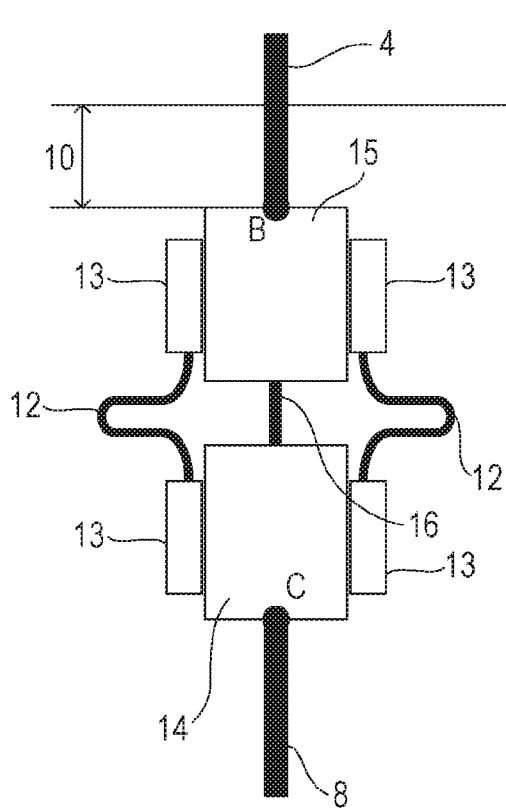
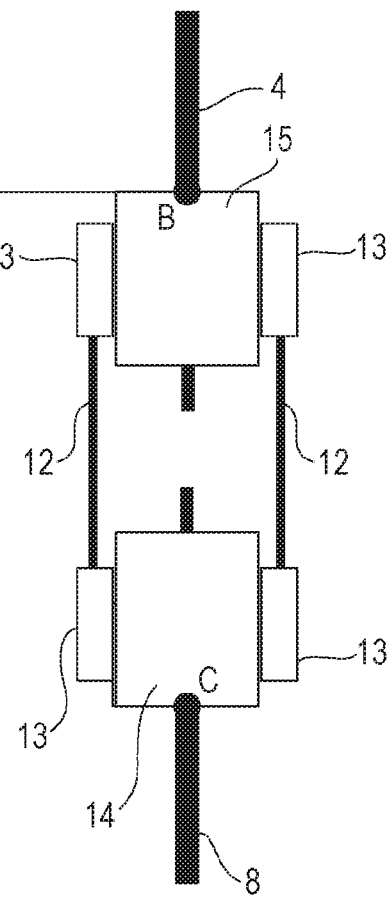

MEDICAL APPARATUS COMPRISING A BENDABLY DEFORMABLE PORTION

CROSS REFERENCE TO RELATED APPLICATIONS

The present application is a Divisional of U.S. patent application Ser. No. 14/403,918, filed on Nov. 25, 2014, which is a National Stage Entry of PCT/JP2013/064562, filed May 21, 2013, which claims priority to Japanese Patent Application No. 2012-124499 filed May 31, 2012, all of which are hereby incorporated by reference herein in its entireties.

TECHNICAL FIELD

The present invention relates to a bendable medical apparatus.

BACKGROUND ART

Medical apparatuses such as endoscopes and electrophysiological catheters that access target sites through internal body structures such as coeloms include insertion portions that are to be inserted into the bodies of patients. The insertion portions of some of such medical apparatuses include bendable portions, with which the insertion portions can move along internal body structures. The medical apparatuses are guided to various sites of human bodies by such bendable functions. As a result, the success rate of examination and treatment is improved, and the pain or side effects experienced by patients, the use or risk of painkillers, and so forth are reduced.

Exemplary medical apparatuses have bendable structures equipped with operation wires. Such a medical apparatus is bendable by pulling the operation wires with a driving unit. PTL 1 discloses a medical apparatus that is capable of retaining a desired bent shape during a treatment even if any operation wires are broken. In this technology, the shape of the apparatus is retained by securing or releasing the operation wires even if any operation wires are broken on a side of the driving unit with respect to a securing/releasing unit.

In the medical apparatus disclosed by PTL 1, the wires may be broken at unexpected positions while the wires are released.

CITATION LIST

Patent Literature

PTL 1 Japanese Patent Laid-Open No. 2004-261431

SUMMARY OF INVENTION

According to an aspect of the present invention, a medical apparatus includes a bendably deformable portion, a deforming-force-transmitting mechanism that is connected to a part of the bendably deformable portion, and an operation portion that applies a deforming force or a shape retaining force to the bendably deformable portion by controlling a tension applied to the deforming-force-transmitting mechanism. The deforming-force-transmitting mechanism includes a tension reducing mechanism.

Further features of the present invention will become apparent from the following description of exemplary embodiments with reference to the attached drawings.

BRIEF DESCRIPTION OF DRAWINGS

FIG. 5A is a conceptual diagram illustrating a breaker portion and a redundant path of a medical apparatus according to a first exemplary embodiment of the present invention that is in a state where the breaker portion is continuous.

FIG. 5B is a conceptual diagram illustrating the breaker portion and the redundant path of the medical apparatus according to the first exemplary embodiment that is in a state where the breaker portion is broken.

DESCRIPTION OF EMBODIMENTS

Figure 1A:
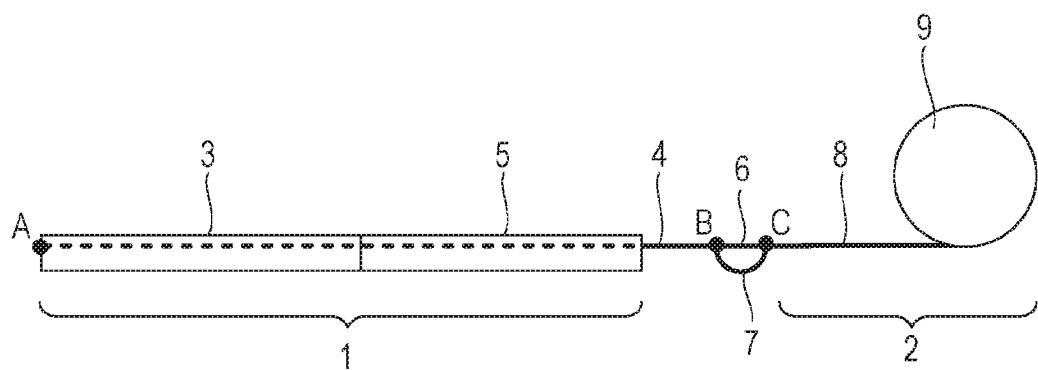
FIG. 1A is a side view illustrating a configuration of a medical apparatus according to a general embodiment of the present invention.

Embodiments of the medical apparatus according to the present invention are summarized as follows when considered from one aspect.

A medical apparatus according to each of embodiments of the present invention includes a bendably deformable portion, a deforming-force-transmitting mechanism that is connected to a part of the bendably deformable portion, and an operation portion that applies a deforming force or a shape retaining force to the bendably deformable portion by controlling a tension applied to the deforming-force-transmitting mechanism. The deforming-force-transmitting mechanism includes a tension reducing mechanism.

The bendably deformable portion is a structure or material a part or the entirety of which is bendable. The part or the entirety of the bendably deformable portion may be inserted into a human body. In such a case, the bendably deformable portion is desired to be deformable while being inside the human body. Typically, the bendably deformable portion has a long side and a short side. The bendably deformable portion is desired to be bendable more easily in a short-side direction than being deformed in a long-side direction.

The deforming-force-transmitting mechanism is connected to a part of the bendably deformable portion. Typically, the deforming-force-transmitting mechanism has a long side and a short side. Typically, one end (one long-side end in many cases) of the deforming-force-transmitting mechanism is connected to the part of the bendably deformable portion. The bendably deformable portion deforms when receiving a force from the deforming-force-transmitting mechanism.

The operation portion applies a deforming force or a shape retaining force to the bendably deformable portion by controlling the tension applied to the deforming-force-transmitting mechanism. For example, in a configuration where one part of the deforming-force-transmitting mechanism and one part of the bendably deformable portion are connected to each other while another part of the deforming-force-transmitting mechanism and the operation portion are connected to each other, the operation portion controls the tension applied to a point between the one part and the other part of the deforming-force-transmitting mechanism. The above connections are not limited to mechanical connections and may be connections utilizing magnetic force or the like.

The tension reducing mechanism may change a distance between the bendably deformable portion and the operation portion by opening a part of the deforming-force-transmitting mechanism when a tension at a predetermined value or higher is applied to the deforming-force-transmitting mechanism. The expression "opening a part of the deforming-force-transmitting mechanism" means that a part of the deforming-force-transmitting mechanism that forms a path through which the deforming force or the shape retaining force is transmitted to the bendably deformable portion opens, disabling the transmission of the deforming force or the shape retaining force to the bendably deformable portion through that path solely. According to an embodiment of the present invention, instead of the open part, a new path (a path having a different length from the path provided before the opening) is provided by another part of the deforming-force-transmitting mechanism. Hence, the deforming force or the shape retaining force continues to be transmitted to the bendably deformable portion.

In an exemplary case where the distance between the bendably deformable portion and the operation portion is changed, the deforming-force-transmitting mechanism may include a first deforming-force-transmitting path, and a second deforming-force-transmitting path that is longer than the first deforming-force-transmitting path. In such a case, when the part of the deforming-force-transmitting mechanism is closed, the deforming force or the shape retaining force from the operation portion is transmitted to the bendably deformable portion through the first deforming-force-transmitting path. Furthermore, when the tension at the predetermined value or higher is applied to the first deforming-force-transmitting path, a part of the first transmitting path opens. After the part of the first transmitting path is open, the deforming force or the shape retaining force from the operation portion is transmitted to the bendably deformable portion through the second transmitting path. The first transmitting path may include a shared part that is shared with a part of the second transmitting path. In such a case, when the tension at the predetermined value or higher is applied to the first deforming-force-transmitting path, a part of the first transmitting path other than the shared part opens.

The medical apparatus according to the above aspect of the present invention may further include a mechanism that detects the opening of the part of the deforming-force-transmitting mechanism. The medical apparatus according to the above aspect of the present invention may further include a mechanism that notifies a user of the opening of the part of the deforming-force-transmitting mechanism.

Embodiments of the present invention are also summarized as the following two typical general embodiments when considered from other aspects.

According to a first general embodiment of the present invention, a medical apparatus includes a bendably deformable portion, a deforming-force-transmitting mechanism that is connected to a part of the bendably deformable portion, and an operation portion that controls a tension applied to the deforming-force-transmitting mechanism. The deforming-force-transmitting mechanism includes a first portion including a wire or a group of wires that are connected in parallel, a second portion including a group of wires that are connected in parallel, and a third portion including a wire or a group of wires that are connected in parallel. The first portion, the second portion, and the third portion are connected in series. At least one of the wires of the second portion has a different length from the others. At least a shortest one of the wires of the second portion includes a part having a smaller tensile breaking strength than all of the other wires included in the deforming-force-transmitting mechanism.

According to a second general embodiment of the present invention, a medical apparatus includes a bendably deformable portion, a deforming-force-transmitting mechanism that is connected to a part of the bendably deformable portion, and an operation portion that controls a tension applied to the deforming-force-transmitting mechanism. The deforming-force-transmitting mechanism includes a first portion including a wire or a group of wires that are connected in parallel, a second portion including a wire or a group of wires that are connected in parallel, and a third portion including a wire or a group of wires that are connected in parallel. The first portion, the second portion, and the third portion are connected in series. All of the wires included in the second portion each have a part having a smaller tensile breaking strength than all of the wires included in the first portion and the third portion. The medical apparatus further includes a tension maintaining member. If all of the wires included in the second portion are broken, the tension maintaining member maintains a tension applied to the first portion and a tension applied to the third portion at substantially the same values as those obtained before the breakage.

The wires may be connected to one another directly or via other members.

The term "wire" represents, in short, a long bendable member and is a concept that encompasses materials that are commonly called thread, cord, wire, and the like.

Typically, the "part having a smaller tensile breaking strength" can be determined on the basis of comparison in terms of the cross sections of the wires. In a case where the tension applied to the deforming-force-transmitting mechanism is experimentally increased, the part that breaks first is determined as the "part having a smaller tensile breaking strength".

Figure 1B:
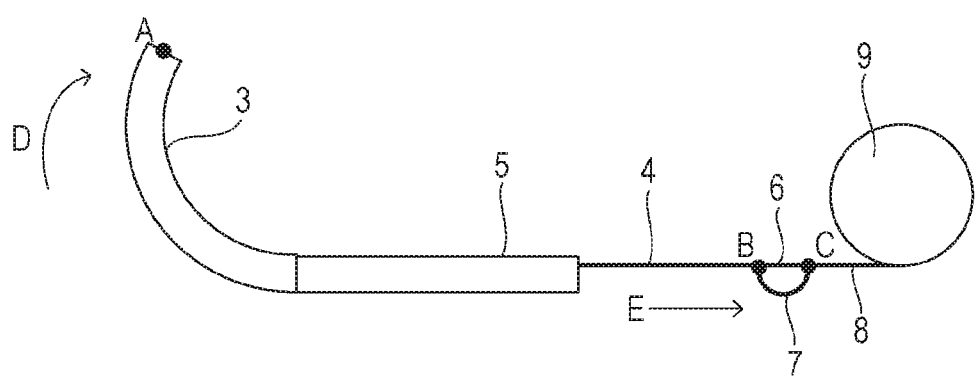
FIG. 1B is a side view illustrating a movement of the medical apparatus according to the general embodiment.

The general embodiments, mainly, the first general embodiment, will now be described more specifically, including modifications thereof. A medical apparatus according to the first general embodiment is configured as illustrated in FIGS. 1A and 1B. FIG. 1A is a side view of the medical apparatus according to the first general embodiment and illustrates the relationship among elements included in the medical apparatus. The medical apparatus according to the first general embodiment includes an insertion portion 1 as the bendably deformable portion. The insertion portion 1 is insertable into a narrow space such as a coelom. The distal end of the insertion portion 1 corresponds to point A. The insertion portion 1 has a round columnar shape whose long-side direction corresponds to a virtual line connecting point A and point B and whose short-side direction is perpendicular to the long-side direction. Hereinafter, a side of the insertion portion 1 that is nearer to point A is referred to as distal side, and the other side of the insertion portion 1 that is nearer to point B is referred to as proximal side. If an image pickup device, an illumination device, and so forth are provided at the distal end A of the insertion portion 1, the medical apparatus functions as an endoscope. If an electrode is provided at the distal end A of the insertion portion 1, the medical apparatus functions as an electrophysiological catheter. The medical apparatus according to the first general embodiment further includes, as the deforming-force-transmitting mechanism, a series of a driving wire 8, a breaker portion 6 including a wire, a redundant path 7 including a wire, and a controlling wire 4 that are connected to one another. As illustrated in FIGS. 1A and 1B, the wire forming the breaker portion 6 and the wire forming the redundant path 7 are connected in parallel as a block. The controlling wire 4 and the driving wire 8 are connected in series with the block. The controlling wire 4 is on the distal side and the driving wire 8 is on the proximal side with respect to the block. The block including the wire forming the breaker portion 6 and the wire forming the redundant path 7 that are connected in parallel corresponds to the second portion. The controlling wire 4 and the driving wire 8 correspond to the first portion and the third portion, respectively. One end of the controlling wire 4 is secured at the distal end A, and the other end of the controlling wire 4 is connected to point B. The controlling wire 4 is a bendable wire capable of transmitting tension and extends through the insertion portion 1 as illustrated by the dotted line in FIG. 1A. The insertion portion 1 has a guide hole (not illustrated) that allows a part of the controlling wire 4 illustrated by the dotted line to move in the long-side direction of the controlling wire 4. The controlling wire 4 passes through the insertion portion 1 at a position deviating from the center of a cross section of the insertion portion 1, the cross section being taken in a direction perpendicular to the long-side direction. The breaker portion 6 and the redundant path 7 that are connected in parallel extend between point B and point C. The driving wire 8 is connected to point C and to a driving pulley 9. The driving wire 8 and the driving pulley 9 in combination function as a driving unit 2. The driving pulley 9 is connected to a power source (not illustrated). A combination of the driving pulley 9 and the power source corresponds to the operation portion. A pulling force generated by the power source is transmitted to the driving unit 2, the breaker portion 6 (or the redundant path 7), and the controlling wire 4 in that order. FIG. 1A illustrates a state where the breaker portion 6 is not broken, that is, the breaker portion 6 is continuous. In the state where the breaker portion 6 is continuous, the breaker portion 6 transmits the pulling force to the controlling wire 4. If the breaker portion 6 is broken in such a manner as to be described below, the redundant path 7 transmits the pulling force to the controlling wire 4.

The insertion portion (bendably deformable portion) 1 includes a bendable portion 3 that is bendable and an unbendable portion 5 that is substantially unbendable. The bendable portion 3 is bendable by pulling the controlling wire 4. The unbendable portion 5 does not substantially bend even by pulling the controlling wire 4. As illustrated in FIGS. 1A and 1B, the bendable portion 3 and the unbendable portion 5 are provided on the distal side and the proximal side, respectively, of the insertion portion 1. The unbendable portion 5 is a stiff portion that does not substantially bend or a flexible portion that has a higher stiffness in the bending direction than the bendable portion 3. The expression "substantially unbendable" used herein means that the stiffness in the bending direction is about 100 times or greater than that of the bendable portion 3.

As described above, the driving unit 2 includes the driving wire 8 and the driving pulley 9. The driving pulley 9 is connected to the power source. When the driving pulley 9 rotates, the driving wire 8 is wound up around the driving pulley 9 and is pulled. The driving wire 8 is made of a material that transmits the pulling force, or a bendable wire material that transmits tension. The driving unit 2 may alternatively have another configuration that transmits the pulling force generated by the power source. For example, the driving unit 2 may be a pushable/pullable columnar member.

A bending movement of the medical apparatus according to the first general embodiment will now be described with reference to FIG. 1B. The driving pulley 9 winds up the driving wire 8 in a direction of arrow E, whereby the breaker portion 6 and the controlling wire 4 are pulled. The controlling wire 4 is secured at the distal end A of the insertion portion 1 and passes through a position deviating from the cross-sectional center of the insertion portion 1. Hence, the tension produced by the pulling of the controlling wire 4 acts as a torque that bends the bendable portion 3 in a direction of arrow D. With such a bending torque, the bendable portion 3 bends as illustrated in FIG. 1B. If the length of the driving wire 8 to be wound around the driving pulley 9 is adjusted, the magnitude of the bending torque is adjusted correspondingly. In this manner, the bending movement of the bendable portion 3 is controlled.

Figure 2A:
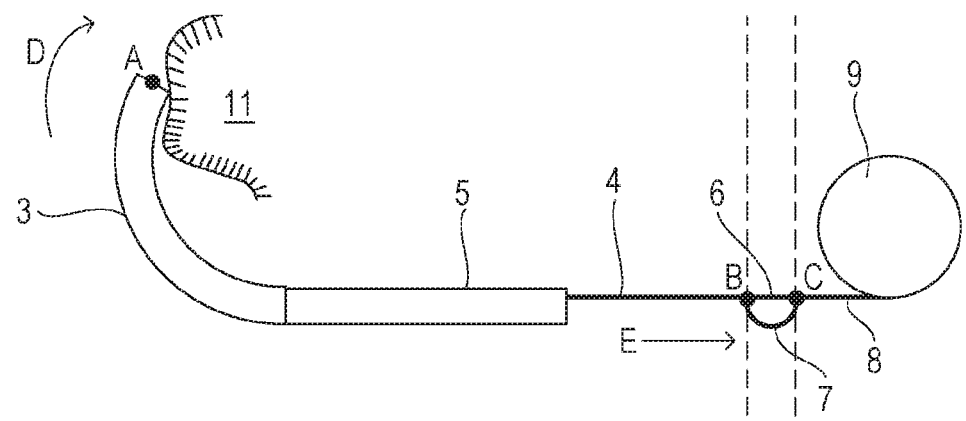
FIG. 2A is a conceptual diagram illustrating a state where a breaker portion of the medical apparatus according to the general embodiment is continuous.

Behaviors of the breaker portion 6 and the redundant path 7 will now be described with reference to FIGS. 2A and 2B, which illustrate a state where the breaker portion 6 is continuous and a state where the breaker portion 6 is broken, respectively. The state illustrated in FIG. 2A is a normal use state. As illustrated in FIG. 2A, when the controlling wire 4 is pulled in the direction of arrow E, the controlling wire 4 undergoes the bending movement in the direction of arrow D. In this state, an environment 11 such as body tissues is in contact with the distal end A. If the controlling wire 4 in this state is further pulled in the direction of arrow E, the distal end A is strongly pressed against the environment 11. Moreover, since a high tension is applied to the elements forming the deforming-force-transmitting mechanism, the elements may be broken. Such a situation is avoidable with the medical apparatus according to the first general embodiment if the breaking strength of the breaker portion 6 is set appropriately. The breaking strength of the breaker portion 6 is set to a value smaller than the breaking strength of the controlling wire 4. Hence, the breaker portion 6 breaks before the tension reaches the breaking strength of the controlling wire 4. Thus, breakage of the deforming-force-transmitting mechanism at an unexpected position is avoided.

If the stress that is allowable by the environment 11 is smaller than the breaking strength of the controlling wire 4, the breaking strength of the breaker portion 6 may be set to a value that does not exceed the allowable stress. In such a case, the influence upon the environment 11 is reduced.

The breaker portion 6 is allowed to be broken at any position between point B and point C. That is, the breaker portion 6 may be broken at point B or point C. For example, the driving wire 8, the redundant path 7, and the controlling wire 4 may be provided as a piece of wire, in parallel with which the breaker portion 6 may be connected. In such a configuration, the breaker portion 6 tends to be broken at point B or point C.

Figure 2B:
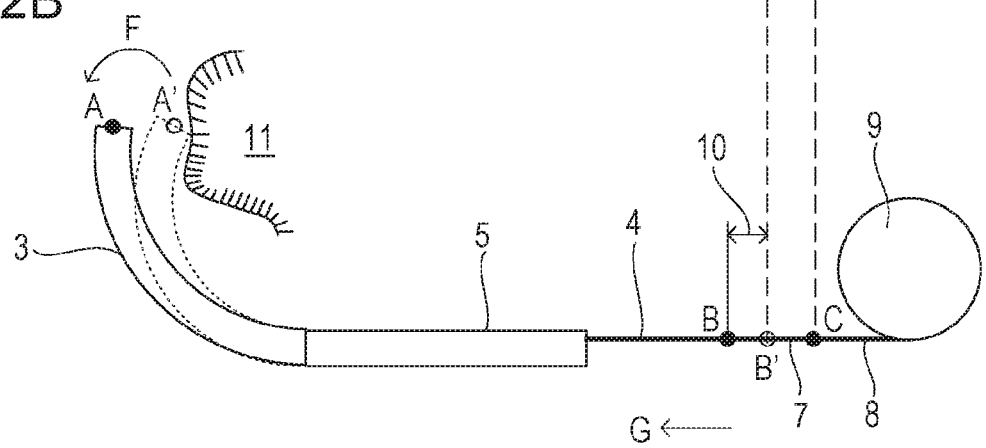
FIG. 2B is a conceptual diagram illustrating a state where the breaker portion of the medical apparatus according to the general embodiment is broken.

FIG. 2B illustrates a state where the breaker portion 6 is broken. If a tension that exceeds the breaking strength of the breaker portion 6 is applied to the breaker portion 6, the breaker portion 6 breaks. Once the breaker portion 6 is broken, the redundant path 7 transmits the tension from the driving wire 8 to the controlling wire 4 as illustrated in FIG. 2B. The redundant path 7 may be made of a bendable wire material that transmits tension, as with the controlling wire 4. In the state illustrated in FIG. 2A, the redundant path 7 is connected to point B and point C with some slack. In the state illustrated in FIG. 2B, the redundant path 7 between point B and point C is stretched with a tension applied thereto so as to transmit the pulling force. When the breaker portion 6 is continuous, the distance between the controlling wire 4 and the driving wire 8 is B'-C. When the breaker portion 6 is broken, the distance between the controlling wire 4 and the driving wire 8 is B-C. The difference between the distance B-C and the distance B'-C is hereinafter referred to as avoiding distance 10. As described above, when the breaker portion 6 breaks, the controlling wire 4 automatically moves in a direction of arrow G by the avoiding distance 10. With the movement of the controlling wire 4 in the direction of arrow G, the distal end A undergoes an avoiding movement from point A' to point A (in a direction of arrow F), avoiding the application of a large pressing force to the environment 11. The avoiding distance 10 is set to a value shorter than a length by which the bendable portion 3 moves so as to return to its natural position (the position taken before the controlling wire 4 is pulled). Therefore, if another environment 11 such as body tissues is present on a side toward which the bendable portion 3 undergoes the avoiding movement (in the direction of arrow F), the application of a large pressing force to the other environment 11 is also avoided. In this manner, at the moment the breaker portion 6 breaks, the distal end A automatically undergoes the avoiding movement. After the distal end A undergoes the avoiding movement, the redundant path 7 in replacement transmits the pulling force transmitted from the driving wire 8. Therefore, the bendable portion 3 remains controllable in the same manner as in the state where the breaker portion 6 is continuous, and the bendable portion 3 is easily removable from the human body.

Behaviors of the breaker portion 6 and the redundant path 7 in another configuration will now be described with reference to FIGS. 3A and 3B, which illustrate a state where a breaker portion 6B is continuous and a state where the breaker portion 6B is broken, respectively. In the configuration illustrated in FIGS. 3A and 3B, two independent systems are provided each including a controlling wire 4A or 4B, a breaker portion 6A or 6B, a redundant path 7A or 7B, a driving wire 8A or 8B, and a driving pulley 9A or 9B. In this configuration, the bendable portion 3 is bendable in two opposite directions including the direction illustrated in FIGS. 3A and 3B. In FIG. 3B, the system including the controlling wire 4A, the breaker portion 6A, the redundant path 7A, the driving wire 8A, and the driving pulley 9A is not illustrated.

To prevent the controlling wires 4A and 4B from slacking during the operation of the medical apparatus, the same pre-tension is applied to the controlling wires 4A and 4B before bending is performed. FIG. 3A illustrates a state where the bendable portion 3 has been bent by pulling the controlling wire 4A and is retained in that bent state. That is, the driving pulleys 9A and 9B are fixed at the respective positions illustrated in FIG. 3A.

Figure 3A:
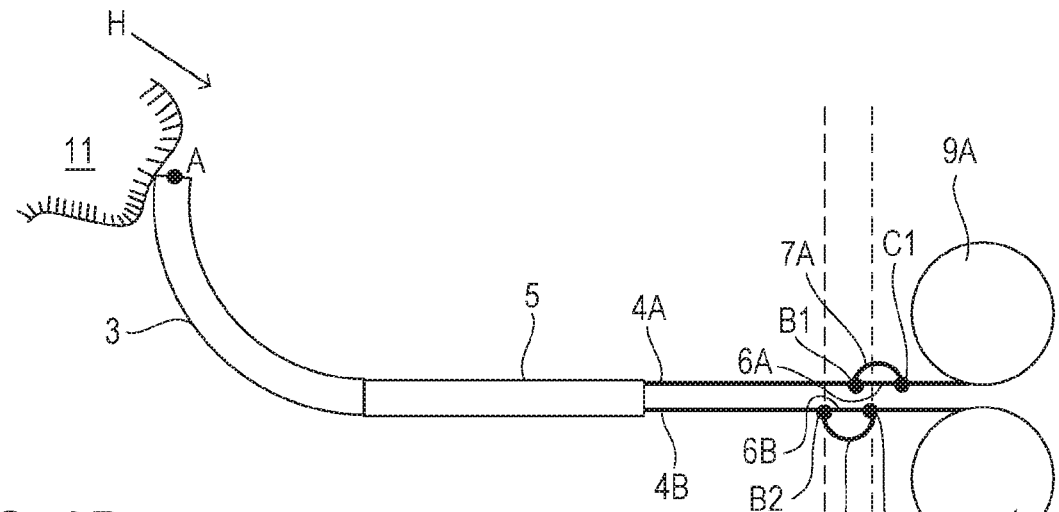
FIG. 3A is a conceptual diagram illustrating a state where a breaker portion of a medical apparatus according to a first modification of the general embodiment of the present invention is continuous.
Figure 3B:
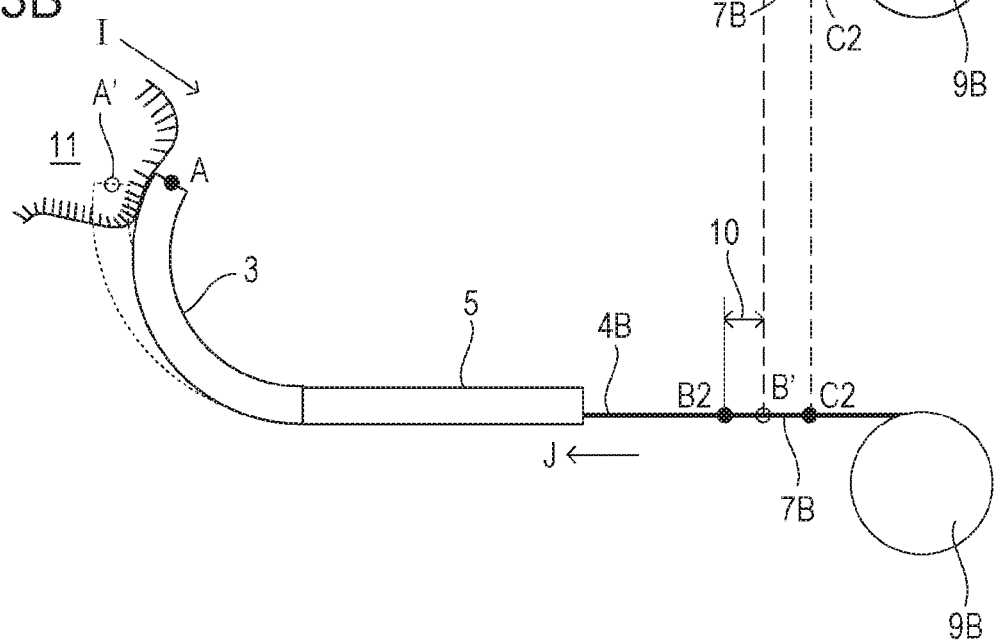
FIG. 3B is a conceptual diagram illustrating a state where the breaker portion of the medical apparatus according to the first modification of the general embodiment is broken.

In FIG. 3A, the environment 11 that is moving has come into contact with the distal end A. Such a movement of the environment 11 may occur with, for example, an unexpected deformation of body tissues. That is, the distal end A may be pushed in a direction of arrow H by the environment 11. In the case illustrated in FIG. 3A also, the environment 11 may be influenced or the controlling wire 4B may break with an excessive load. In the configuration illustrated in FIG. 3A, the controlling wires 4A and 4B each include a corresponding one of the breaker portions 6A and 6B and a corresponding one of the redundant paths 7A and 7B. In the state illustrated in FIG. 3A, the tension applied to the controlling wire 4B increases, and the breaker portion 6B breaks. In FIG. 3B, the breaker portion 6B is broken. When the breaker portion 6B breaks, the controlling wire 4B automatically moves in a direction of arrow J by the avoiding distance 10. Hence, even if the environment 11 continues to move in a direction of arrow I, the application of a large stress to the distal end A is avoided while the distal end A is moving from point A' to point A. In this manner, even if the distal end A is pushed by the environment 11, the breaker portion 6B prevents the occurrence of a large load that may be applied to the controlling wire 4B. Furthermore, the redundant path 7B allows the bendable portion 3 to undergo the avoiding movement that prevents the moving environment 11 from being influenced.

Figure 4:
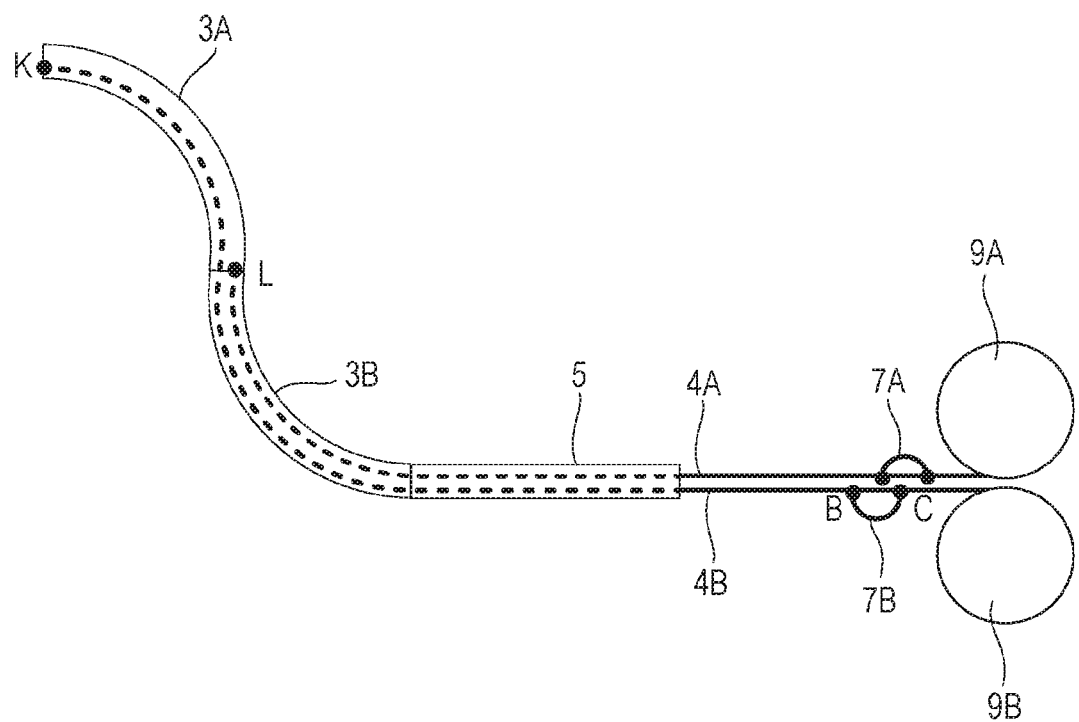
FIG. 4 is a conceptual diagram illustrating a medical apparatus according to a second modification of the general embodiment that includes a plurality of bendable portions.

FIG. 4 illustrates another medical apparatus according to the first general embodiment. As with the configuration illustrated in FIGS. 3A and 3B, the configuration illustrated in FIG. 4 includes two independent systems each including a controlling wire 4A or 4B, a breaker portion 6A or 6B, a redundant path 7A or 7B, a driving wire 8A or 8B, and a driving pulley 9A or 9B. In addition, the insertion portion 1 includes two bendable portions 3A and 3B. The controlling wire 4A is secured at point L and is capable of bending the bendable portion 3B. The controlling wire 4B is secured at point K and is capable of bending both of the bendable portions 3A and 3B. Thus, the bendable portions 3A and 3B are bendable by desired amounts, respectively, by adjusting the tensions applied to the respective controlling wires 4A and 4B. Therefore, as illustrated in FIG. 4, the bendable portions 3A and 3B are simultaneously bendable in opposite directions, respectively. In this configuration also, the medical apparatus can undergo the avoiding movement in the situation described above referring to FIGS. 2A to 3B. Particularly, the controlling wires 4A and 4B in this configuration are provided for the different bendable portions 3A and 3B, and loads allowable by the controlling wires 4A and 4B are different. Therefore, if the breaking strengths of the breaker portions 6A and 6B (not illustrated but connected in parallel with the redundant paths 7A and 7B, respectively) are adjusted, the breaker portions 6A and 6B can be made to function with respective desired loads.

The relationship between the length of pulling the controlling wire 4 and the length of travel of the distal end (point K) also differs between the controlling wires 4A and 4B. Therefore, if the lengths of the redundant paths 7A and 7B are adjusted, the avoiding distance 10 and the displacement of the distal end K resulting from the avoiding movement can be set to desired values, respectively.

As described above, each of the above medical apparatuses according to the first general embodiment of the present invention includes the breaker portion 6 and the redundant path 7. Therefore, the controlling wire 4 is prevented from breaking, and the influence upon the environment 11 such as peripheral tissues is reduced. Even if the controlling wire 4 includes a plurality of wires, the breaker portion 6 and the redundant path 7 can be provided for each of the controlling wires 4 independently. Hence, the loads allowable by the respective controlling wires 4 and the length of avoiding movement of the distal end A or K can be set for the individual breaker portions 6 and the individual redundant paths 7.

EXEMPLARY EMBODIMENTS

More specific embodiments of the present invention will now be described. The following exemplary embodiments do not limit the present invention in any way.

First Exemplary Embodiment

A first exemplary embodiment of the present invention will now be described with reference to FIGS. 5A and 5B. The first exemplary embodiment corresponds to the first general embodiment described above. More specifically, FIGS. 5A and 5B illustrate elements according to the first exemplary embodiment that correspond to the breaker portion 6 and the redundant path 7 illustrated in FIGS. 1A to 4. FIG. 5A illustrates a state where an element corresponding to the breaker portion 6 is continuous. FIG. 5B illustrates a state where the element corresponding to the breaker portion 6 is broken.

The controlling wire 4 is secured by a controlling wire anchor 15, which is also referred to as controlling wire holder. The driving wire 8 is secured by a driving wire anchor 14, which is also referred to as driving wire holder. Points B and C illustrated in FIGS. 5A and 5B correspond to points B and C illustrated in FIGS. 1A and 1B. The driving wire anchor 14 and the controlling wire anchor 15 are connected to each other with a breaker wire 16, which corresponds to the breaker portion 6. The breaker wire 16 has a smaller diameter than the controlling wire 4 and the driving wire 8. Therefore, the breaker wire 16 has a low breaking strength than the controlling wire 4 and the driving wire 8.

The driving wire anchor 14 and the controlling wire anchor 15 are connected to each other also with redundant wires 12 and redundant wire anchors 13, which correspond to the redundant path 7. The redundant wire anchors 13 are also referred to as redundant wire holders. The redundant wires 12 each have some slack and are horizontally symmetrical to each other in the state illustrated in FIG. 5A. In the first exemplary embodiment, the controlling wire 4 is made of a superelastic titanium-nickel alloy, and the driving wire 8 and the breaker wire 16 are made of stainless steel.

Referring to FIG. 5B, when the breaker wire 16 breaks, the redundant wires 12 each having some slack are stretched. Hence, the controlling wire 4 moves in a direction away from point C by the avoiding distance 10. In this manner, with the breaking strength of the breaker wire 16 being as a threshold, the avoiding movement is realized without any overload on the controlling wire 4. Thereafter, the redundant wires 12 allow the pulling force transmitted from the driving wire 8 to be transmitted to the controlling wire 4. Hence, the bendable portion 3 continues to be operable and is removable from the human body.

The presence of the driving wire anchor 14 and the controlling wire anchor 15 makes it possible to exchange the breaker wire 16 solely. Therefore, even if the insertion portion 1 has an overload, the medical apparatus can be repaired easily. Furthermore, the redundant wire anchors 13 may be detachable from the driving wire anchor 14 and the controlling wire anchor 15 via screws, hooks or the like. Such a configuration facilitates exchanging of the redundant wires 12 and changing of the avoiding distance 10.

The elements corresponding to the breaker portion 6 and the redundant path 7 are all wires and are therefore bendable freely. Hence, the path from the controlling wire 4 to the driving pulley 9 can be set freely. Particularly, in a case where the outside diameter of the insertion portion 1 is small and the gap between adjacent ones of a plurality of driving pulleys 9 is larger than the gap between adjacent ones of a plurality of controlling wires 4 provided in correspondence with the driving pulleys 9, the freedom in setting the above path is advantageous.

The controlling wire anchor 15 may have optical or magnetic reference marks or graduations. By optically or magnetically reading the positions of such marks (or graduations), the length by which the controlling wire 4 has been pulled can be detected. Furthermore, any breakage of the breaker wire 16 can be detected, whereby the application of a load exceeding the allowable stress can be detected.

Second Exemplary Embodiment

A second exemplary embodiment of the present invention will now be described with reference to FIGS. 6A, 6B, 7A, and 7B. The second exemplary embodiment corresponds to the second general embodiment described above. Elements having the same functions as those described in the first exemplary embodiment are denoted by the corresponding reference numerals, and description thereof is thus omitted.

Figure 6A:
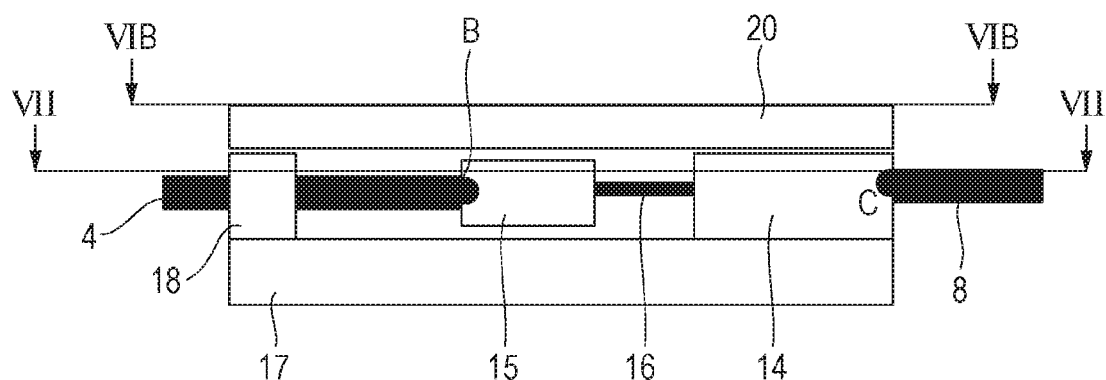
FIG. 6A is a sectional view illustrating a breaker portion and a redundant path of a medical apparatus according to a second exemplary embodiment of the present invention.
Figure 6B:
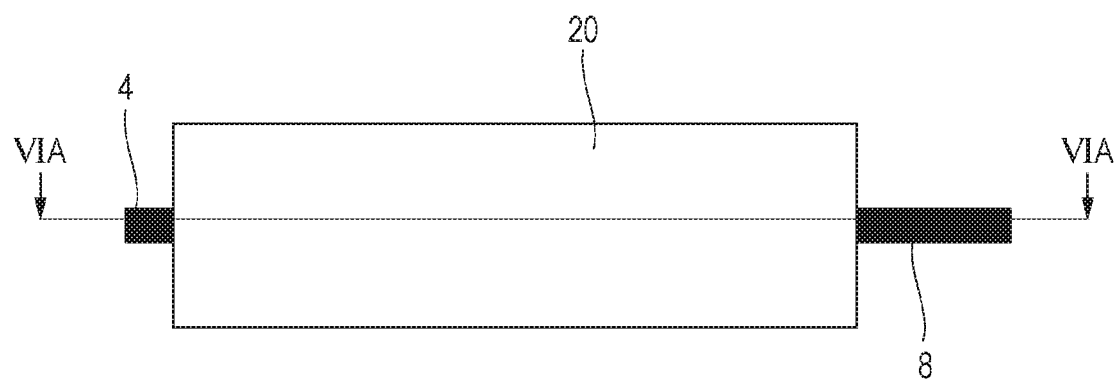
FIG. 6B is a top view illustrating the breaker portion and the redundant path of the medical apparatus according to the second exemplary embodiment.

FIGS. 6A and 6B are a sectional view and a top view, respectively, of elements according to the second exemplary embodiment that correspond to the breaker portion 6 and the redundant path 7. FIG. 6A is taken along line VIA-VIA illustrated in FIG. 6B. FIG. 6B is taken along line VIB-VIB illustrated in FIG. 6A.

The second exemplary embodiment differs from the first exemplary embodiment in elements corresponding to the redundant path 7. In the second exemplary embodiment, the elements corresponding to the redundant path 7 include a link portion 17 and a stopper portion 18, which in combination correspond to the tension maintaining member described above.

The driving wire anchor 14 is secured to the link portion 17. The stopper portion 18 is secured to the link portion 17. The link portion 17 and the stopper portion 18 are made of highly stiff materials. In the second exemplary embodiment, the link portion 17 and the stopper portion 18 are made of stainless steel.

The controlling wire 4 extends through the stopper portion 18. The controlling wire 4 is movable with respect to the stopper portion 18. The controlling wire anchor 15 is provided above the link portion 17. A cover 20 is provided as illustrated in FIGS. 6A and 6B and guides the controlling wire anchor 15 to be movable only along a virtual line passing through point C and point B.

Figure 7A:
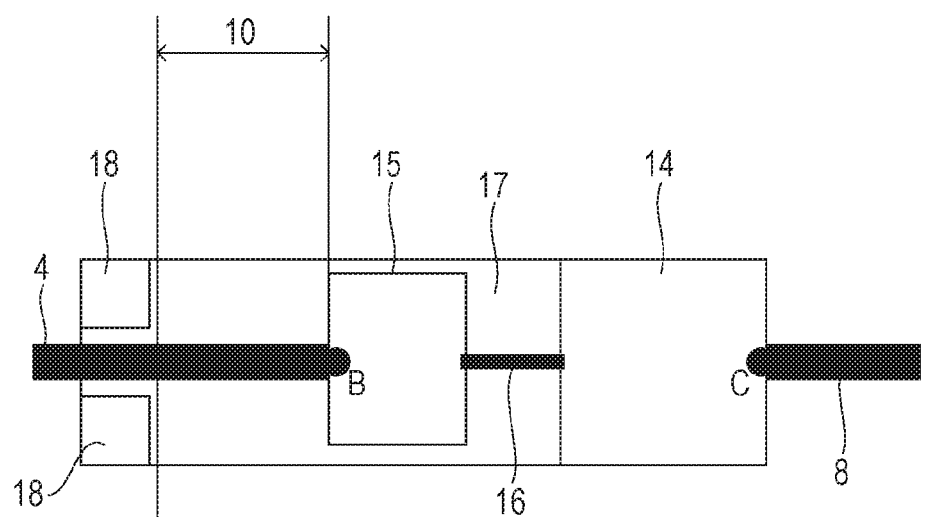
FIG. 7A is a sectional view illustrating a state where the breaker portion of the medical apparatus according to the second exemplary embodiment is continuous.
Figure 7B:
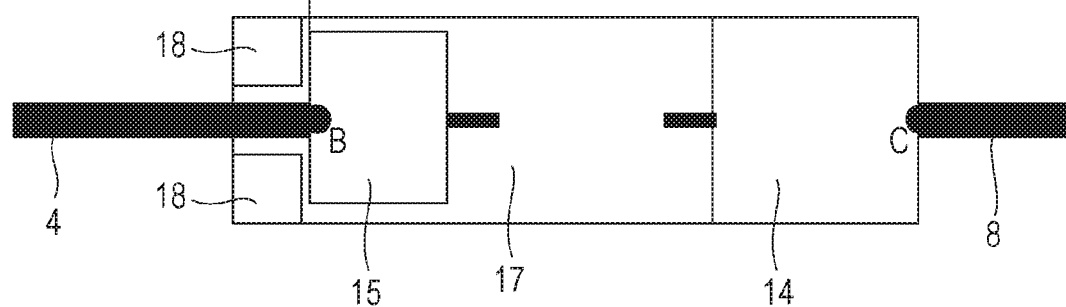
FIG. 7B is a sectional view illustrating a state where the breaker portion of the medical apparatus according to the second exemplary embodiment is broken.

Behaviors of the above elements according to the second exemplary embodiment will now be described with reference to FIGS. 7A and 7B. FIGS. 7A and 7B are sectional views both taken along line VII-VII illustrated in FIG. 6A and illustrate a state where the breaker wire 16 is continuous and a state where the breaker wire 16 is broken, respectively. As illustrated in FIG. 7A, when the breaker wire 16 is continuous, the controlling wire anchor 15 is spaced apart from the stopper portion 18 by the avoiding distance 10. As illustrated in FIG. 7B, when the breaker wire 16 is broken, there is no gap between the controlling wire anchor 15 and the stopper portion 18 and the space between the controlling wire anchor 15 and the driving wire anchor 14 increases by the avoiding distance 10. In this manner, the controlling wire 4 is movable by the avoiding distance 10 as illustrated in FIGS. 7A and 7B. In the state illustrated in FIG. 7B where the breaker wire 16 is broken, the controlling wire anchor 15 is stopped by the stopper portion 18. Hence, the pulling force transmitted from the driving wire 8 is transmitted to the controlling wire 4.

Since the link portion 17 and the stopper portion 18 are highly stiff, the avoiding distance 10 is determined accurately. Particularly, the amount of deformation of the stopper portion 18 that occurs when the controlling wire anchor 15 collides with the stopper portion 18 is negligibly small compared with the avoiding distance 10. Therefore, the avoiding distance 10 is determined accurately.

Since the link portion 17 and the cover 20 cover the breaker wire 16, the breaker wire 16 is prevented from breaking with an unexpected external force. For example, an unintentional touch on the breaker wire 16 during disassembling work, adjusting work, or the like is prevented. In addition, in the state where the breaker wire 16 is continuous, foreign matter is prevented from unexpectedly getting caught between the stopper portion 18 and the controlling wire anchor 15. Hence, the avoiding movement is assuredly realized in response to the breakage of the breaker wire 16.

Figure 8A:
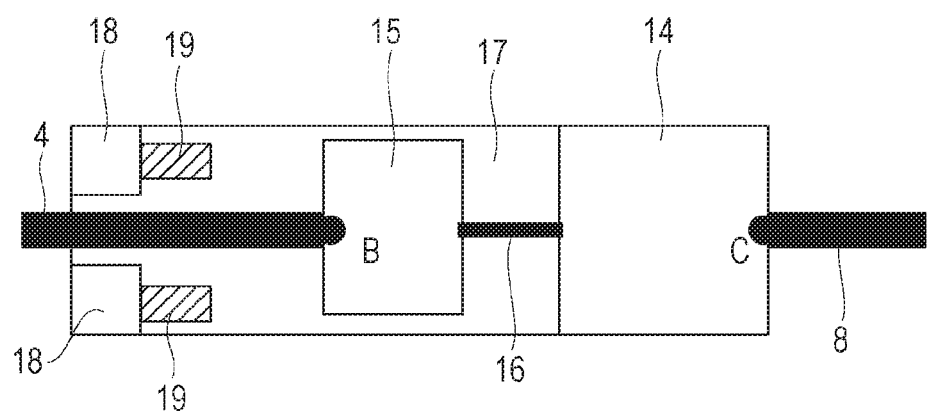
FIG. 8A is a sectional view illustrating a state where a breaker portion of a medical apparatus according to a modification of the second exemplary embodiment is continuous.
Figure 8B:
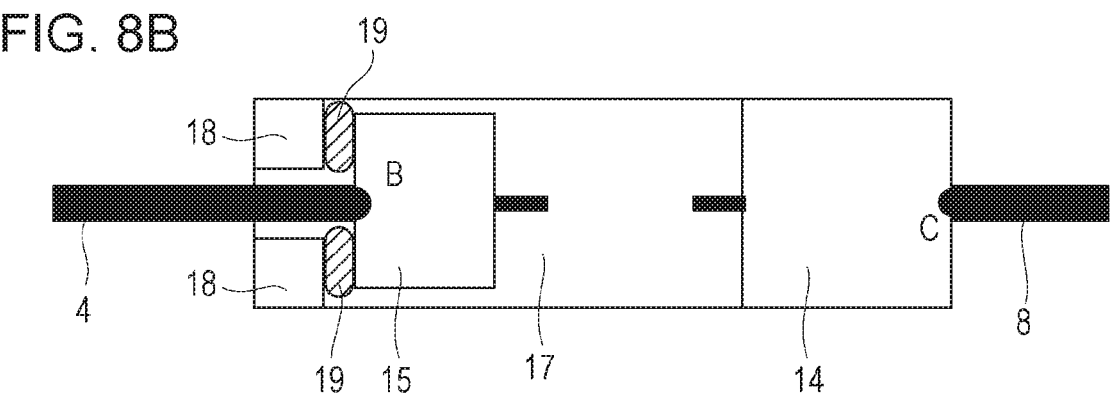
FIG. 8B is a sectional view illustrating a state where the breaker portion of the medical apparatus according to the modification of the second exemplary embodiment is broken.

A modification of the second exemplary embodiment will now be described with reference to FIGS. 8A and 8B. FIGS. 8A and 8B illustrate the modification in which a damper member 19 is added to the configuration illustrated in FIGS. 7A and 7B. The damper member 19 is also a part of the tension maintaining member described above. FIGS. 8A and 8B illustrate a state where the breaker wire 16 is continuous and a state where the breaker wire 16 is broken, respectively. As illustrated in FIG. 8A, the damper member 19 is provided between the controlling wire anchor 15 and the stopper portion 18. In this modification, the damper member 19 is secured to the stopper portion 18. The damper member 19 is in a form similar to the stopper portion 18. The controlling wire 4 is movable with respect to the damper member 19. The damper member 19 may be made of an elastomer based on nylon, urethane, or the like. In this modification, the damper member 19 is made of urethane elastomer.

When the breaker wire 16 breaks, the damper member 19 is sandwiched between the controlling wire anchor 15 and the stopper portion 18 as illustrated in FIG. 8B. In this state, the damper member 19 absorbs the impact of collision of the controlling wire anchor 15 against the stopper portion 18. Thus, the rate of change in the pulling force that occurs at the collision of the controlling wire anchor 15 against the stopper portion 18 is reduced. Furthermore, in a case where the rate of change in the pulling force is nearly the same as or greater than the frequency of vibration in any of various resonance modes generated in the bendable portion 3, unnecessary excitation of resonance that may occur in the insertion portion 1 is suppressed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-124499, filed May 31, 2012, which is hereby incorporated by reference herein in its entirety.

REFERENCE SIGNS LIST 1 insertion portion
2 driving unit
3, 3A, 3B bendable portion
4, 4A, 4B controlling wire
5 unbendable portion
6 breaker portion
7, 7A, 7B redundant path
8 driving wire
9, 9A, 9B driving pulley
10 avoiding distance
11 environment
12 redundant wire
13 redundant wire anchor
14 driving wire anchor
15 controlling wire anchor
16 breaker wire
17 link portion
18 stopper portion
19 damper member
20 cover

ADVANTAGEOUS EFFECTS OF INVENTION

According to the present invention, breakage of any wires at unexpected positions is prevented with a simple mechanism.

The invention claimed is:
1. A medical apparatus comprising:
a bendably deformable portion;
a deforming-force-transmitting mechanism that is connected to a part of the bendably deformable portion; and
a controller that controls a tension applied to the deforming-force-transmitting mechanism,
wherein the deforming-force-transmitting mechanism includes
a controlling wire including a wire or a group of wires that are connected to the part of the bendably deformable portion;
a controlling wire anchor fixed to an end of the controlling wire;
a breaker;
a driving wire including a wire or a group of wires that transmits a deforming force generated by a power source to the controlling wire, in accordance with a control by the controller; and
a driving wire anchor fixed to an end of the driving wire,
wherein the controlling wire anchor, the breaker, and the driving wire anchor are connected in series, wherein the breaker has a smaller breaking strength than a breaking strength of each of the controlling wire and the driving wire, wherein the medical apparatus further includes a tension maintaining member having a link portion to which the driving wire is secured via the driving wire anchor and a stopper portion secured to the link portion, wherein the stopper portion is configured to limit a movement of the controlling wire anchor away from the driving wire anchor by a predetermined distance, wherein, during a period from a disconnection of the controlling wire anchor and the driving wire anchor by the breaker to a stop of the controlling wire anchor by the stopper portion, the medical apparatus is configured such that the deforming force applied to the controlling wire becomes smaller than the deforming force applied before the disconnection, wherein, after the stop of the controlling wire anchor by the stopper portion, the tension maintaining member is configured to transmit the deforming force generated by the power source from the driving wire to the controlling wire.

2. The medical apparatus according to claim 1, wherein the controlling wire is positioned in such a manner as to deviate from a center of a cross section of the bendably deformable portion.

3. The medical apparatus according to claim 1, wherein the predetermined distance is an avoiding distance that is a distance between a first position of the controlling wire anchor before the breaker brakes and a second position of the controlling wire anchor after the breaker brakes and the controlling wire anchor is stopped by the stopper portion.

4. The medical apparatus according to claim 1, wherein the driving wire is configured to drive to transmit a pulling force from the driving wire to the controlling wire so that the tension maintaining member maintains a tension applied to the controlling wire and a tension applied to the driving wire.

5. The medical apparatus according to claim 1, wherein the driving wire is configured to, in a case where the controlling wire anchor and the driving wire anchor are not connected via the breaker in series, continue to transmit a pulling force from the driving wire to the controlling wire through the tension maintaining member, and wherein the controlling wire anchor is configured to, in a case where the controlling wire anchor and the driving wire anchor are not connected via the breaker in series, eliminate a gap between the controlling wire anchor and the stopper portion and to increase a space between the controlling wire anchor and the driving wire anchor by an avoiding distance.

* * * * *